(12) United States Patent
Shipp

(10) Patent No.: US 6,449,006 B1
(45) Date of Patent: Sep. 10, 2002

(54) LED ILLUMINATION SYSTEM FOR ENDOSCOPIC CAMERAS

(75) Inventor: John I. Shipp, Tullahoma, TN (US)

(73) Assignee: Apollo Camera, LLC, Tullahoma, TN (US)

( * ) Notice: Subject to any disclaimer, the term of this patent is extended or adjusted under 35 U.S.C. 154(b) by 1128 days.

(21) Appl. No.: 08/531,424

(22) Filed: Sep. 21, 1995

Related U.S. Application Data

(60) Division of application No. 08/156,376, filed on Nov. 22, 1993, now abandoned, which is a continuation-in-part of application No. 07/905,278, filed on Jun. 26, 1992, now Pat. No. 5,264,925.

(51) Int. Cl.[7] .............................................. H04N 7/18
(52) U.S. Cl. ........................................ 348/70; 600/101
(58) Field of Search ..................... 348/29, 65, 69–71, 348/76, 271; 362/800; 600/101, 109; H04N 7/18

(56) References Cited

U.S. PATENT DOCUMENTS

| | | | |
|---|---|---|---|
| 4,074,306 A | * 2/1978 | Kakinuma et al. ............. | 348/71 |
| 4,253,447 A | * 3/1981 | Moore et al. .................. | 348/71 |
| 4,631,582 A | * 12/1986 | Nagasaki et al. .............. | 348/69 |
| 4,633,304 A | * 12/1986 | Nagasaki ..................... | 600/109 |
| 4,745,470 A | * 5/1988 | Yabe et al. .................... | 348/76 |
| 4,809,680 A | 3/1989 | Yabe .............................. | 128/6 |
| 4,832,003 A | * 5/1989 | Yabe ........................... | 348/65 |
| 4,868,647 A | * 9/1989 | Uehara et al. ................ | 348/65 |
| 4,879,992 A | * 11/1989 | Nishigaki et al. ............. | 348/65 |
| 4,888,639 A | * 12/1989 | Yabe et al. .................... | 348/69 |
| 4,918,521 A | * 4/1990 | Yabe et al. .................... | 348/76 |
| 4,967,264 A | * 10/1990 | Parulski et al. ............... | 348/271 |
| 5,013,144 A | * 5/1991 | Silverglate et al. ......... | 362/800 |
| 5,034,888 A | * 7/1991 | Uehara et al. ................ | 348/29 |
| 5,142,359 A | * 8/1992 | Yamamori .................... | 348/70 |
| 5,264,925 A | 11/1993 | Shipp et al. .................. | 358/44 |
| 5,379,756 A | * 1/1995 | Pileski et al. ................ | 600/109 |
| 5,423,312 A | * 6/1995 | Siegmund et al. .......... | 600/109 |
| RE35,076 E | * 10/1995 | Nakamura .................... | 348/70 |
| 5,604,531 A | * 2/1997 | Iddan et al. ................. | 600/109 |

* cited by examiner

*Primary Examiner*—Richard Lee
(74) *Attorney, Agent, or Firm*—Waddey & Patterson; I. C. Waddey, Jr.

(57) ABSTRACT

An illumination system for an endoscopic camera has a plurality of light emitting diodes mounted to a substrate. The substrate is adapted for attachment at the distal end of the endoscope. Each LED is contained within a reflector cup which directs the angular dispersion of emitted light toward the object to be viewed.

17 Claims, 11 Drawing Sheets

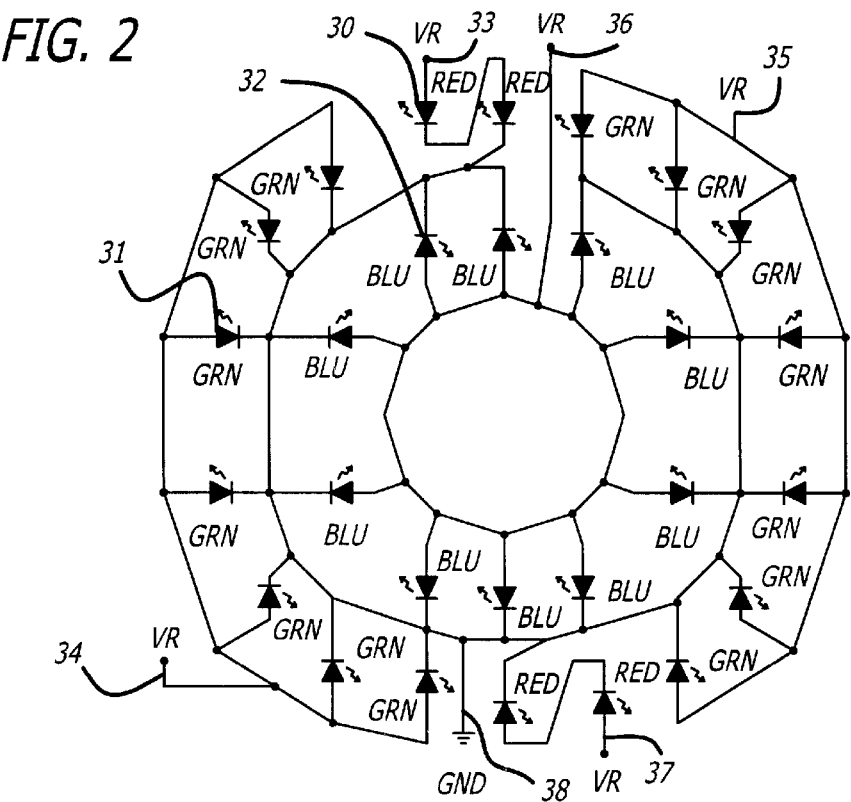
FIG. 2
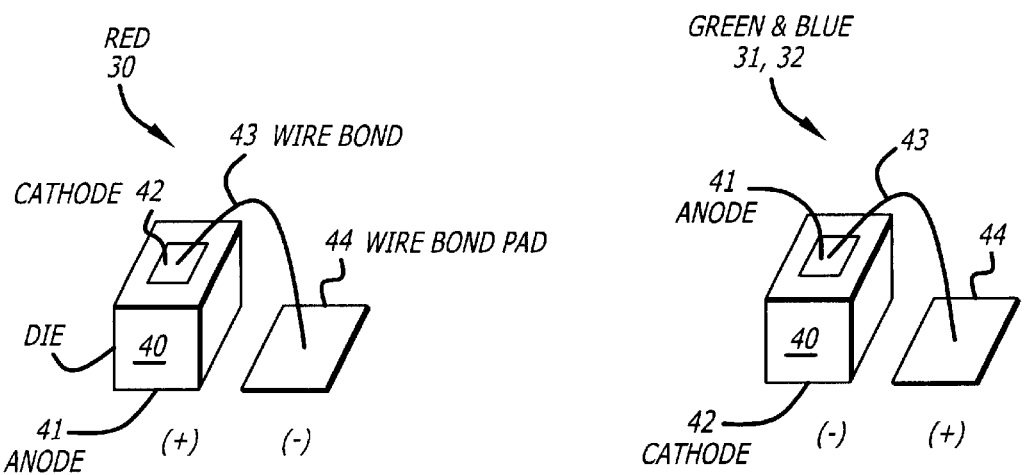
FIG. 3
FIG. 4

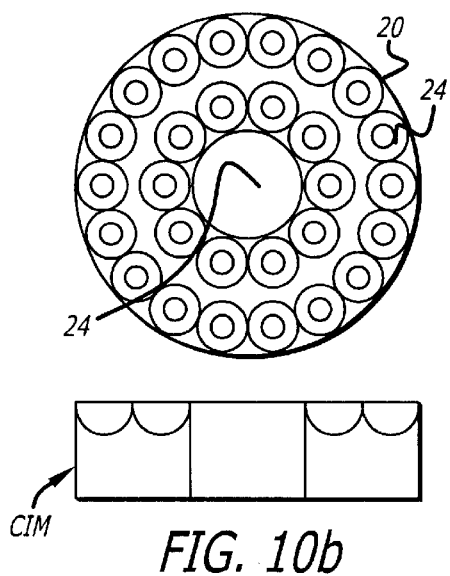
FIG. 10a
FIG. 10b
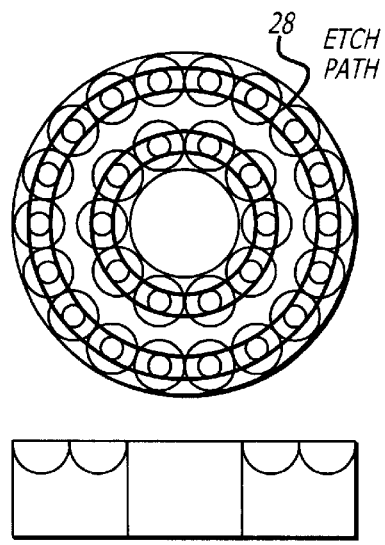
FIG. 11a
FIG. 11b
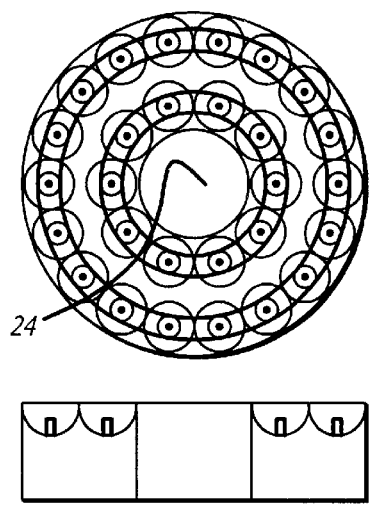
FIG. 12a
FIG. 12b
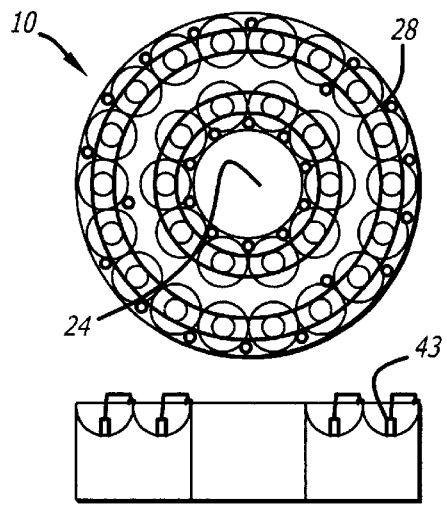
FIG. 13a
FIG. 13b

LED ILLUMINATION SYSTEM FOR ENDOSCOPIC CAMERAS

This is a division of U.S. patent application Ser. No. 08/156,376 for a 'LED Illumination System for Endoscopic Cameras', filed Nov. 22, 1993 now abandoned, which was a continuation-in-part of U.S. patent application Ser. No. 07/905,278 filed Jun. 26, 1992, for 'Single Sensor Video Imaging System and Method Using Sequential Color Object Illumination, now U.S. Pat. No. 5,264,925.

BACKGROUND OF THE INVENTION

The present invention relates generally to light sources used to illuminate body cavities during laparascopic surgery, and more particularly to a light assembly mounted in the distal end of an endoscope which emits white light, or red, blue, and green light within the body cavity during surgery.

Because of varying sizes and geometries, the interiors of various body cavities have different requirements for adequately illuminating them during the use of laparascopic (or endoscopic) cameras. An insufflated abdominal cavity, for example, has a volume of several liters, with the distance from the peritoneum to the liver bed ranging from 5 to 12 centimeters, depending upon the size and obesity of the patient. The geometry of the cavity is such that an angular field of view of between 50 to 80 degrees is desired for observation and illumination. Typical laparascopic surgical procedures necessitate endoscope-to-object distances of 1.5 to 15 centimeters.

Several illumination techniques are employed in the prior art. Where the endoscopic camera system uses white light illumination, a Xenon light source is typically focused onto one end of a flexible fiber optics cable. The other end of the cable is attached to a 90 degree coupling attached to an endoscope, the periphery of which comprises an annular fiber optics bundle terminating at the distal end of the endoscope. Light is emitted from the annular (donut shaped) fiber bundle into the body cavity where a portion of it is reflected and captured by the objective lens of the endoscope and relayed through the center of the scope to the CCD detector array. The white light thus must be separated, after the illumination step, into three primary components, usually red, green, and blue, before it can be processed into a color image by a non-sequential color CCD camera.

Field sequential cameras, on the other hand, utilize light sources which usually are separated into three primary colors prior to illumination of the object. Prior art sequential cameras, such as that described in U.S. Pat. No. 4,631,582 for example, utilize rotating segmented color filters in the path of white light sources, or color filters in the path of sequentially illuminated white strobe lights.

There are several problems associated with the prior art. Most light sources of the prior art are large, cumbersome, and inefficient. Thus, the efficiency of collection and transmission of light from a Xenon tube to the body cavity is poor, often as low as 0.1 percent. It is also difficult to match the angular spread of the light from the fiber optics cable to that of the angular field of view of the objective lens. Either the spread is too large, causing light to fall in areas where it is unusable, or the spread is smaller than the angular field of view of the objective, thereby causing vignetting. Additionally, the light distribution from prior art illumination sources is often a problem. A dark spot generally is located in the center of the picture causing the image quality to be inferior, particularly at close object distances. Also, the fiber optics cable used in prior art illumination devices comes into contact with the sterile zone in the operating room and thus must be re-sterilized before each use. The sterilization process often causes catastrophic damage to, or degrades, the cable. The present invention solves these and other problems characteristic of prior art laparascopic illumination systems.

SUMMARY OF THE INVENTION

An object of the present invention is to provide a system for illuminating body cavities during laparascopic surgery which is optically and energy efficient and which provides the desired angular dispersion of illuminating light.

Another object of the present invention is to eliminate the light-loss, size, and sterilization problems inherent in the use of fiber-optic cables and bundles.

Yet another object of the present invention is to adapt an illumination system for use with a field sequential single sensor video camera or with a sequential chrominance-luminance YC camera system.

In accordance with these and other objectives which will be apparent to those skilled in the art, the present invention comprises an efficient, compact, light source mounted in the distal end of an endoscope, usable with a field sequential single sensor video imaging system such as that described in co-pending U.S. patent application Ser. No. 905,278. A series of four red, fourteen green, and ten blue light emitting diodes (LED's) are mounted and arranged on a ceramic substrate in a circular pattern concentrically around the optical path of the endoscope. A reflector cup surrounds each LED to help control the angular distribution of the emitted light. The LED's are electrically wired to an illumination circuit which causes them to emit red, blue, and green light in synchronization with the field period of a CCD endoscopic camera. Because the LED's are mounted in the distal end of the endoscope, the typical prior art light loss through fiber optics cables and connections is avoided and the need for cable sterilization is eliminated. The LED arrangement uniformly illuminates objects within body cavities with the required angular dispersion. The efficiency of the light source allows for battery operation of the camera and lights making the system much more portable.

BRIEF DESCRIPTION OF THE DRAWINGS

FIG. 2 is a schematic plan view of the LED assembly of FIG. 1, showing the approximate layout of the 28 LED's and power connection points on the substrate.

FIG. 3 is an enlarged view of a red LED chip as used in the present invention, showing its wired connections to the substrate of the illumination means.

FIG. 4 is an enlarged view of a green or blue LED chip as used in the present invention, showing its wired connections to the substrate of the illumination means.

FIG. 6b is a side view of the reflector cup of FIG. 6a.

FIGS. 10a and b are plan and cutaway side views of a second embodiment of the LED assembly of the present invention in which the reflector cups are formed integral to the substrate.

FIGS. 11a and b are plan and cutaway side views of the illumination means of FIG. 10a, after the LED wiring pads have been etched and gold flashed.

FIGS. 12a and b are plan and cutaway side views of the illumination means of FIG. 11a, after mounting of the LED dies to the reflector cups.

FIGS. 13a and b are plan and cutaway side views of the illumination means of FIG. 12, after wiring bonding of the anodes or cathodes of the LED's to the wiring pads.

DESCRIPTION OF THE PREFERRED EMBODIMENT

Figure 1:
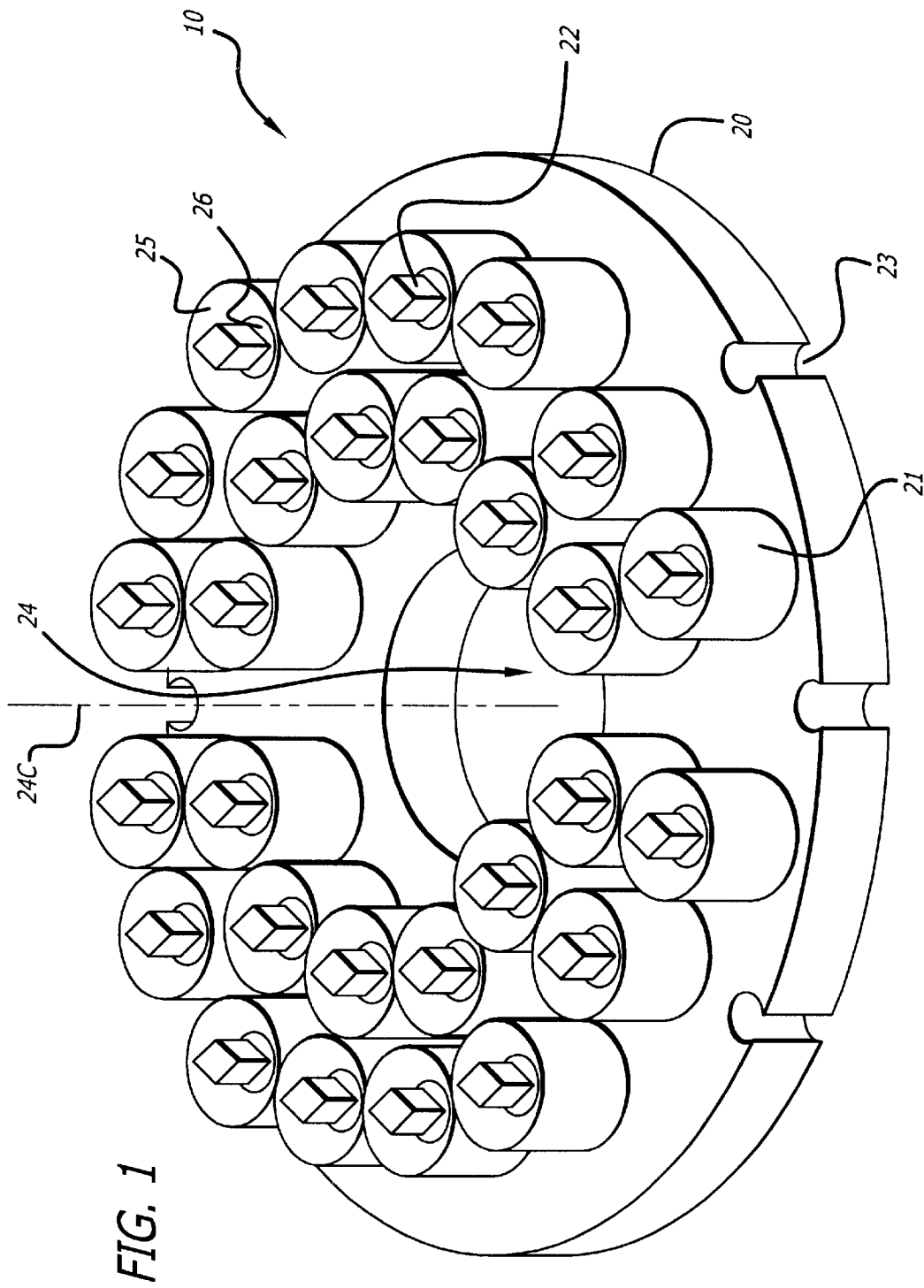
FIG. 1 is an oblique view of a first embodiment of the present invention in which the illumination means is a distally mounted LED assembly.
Figure 8:
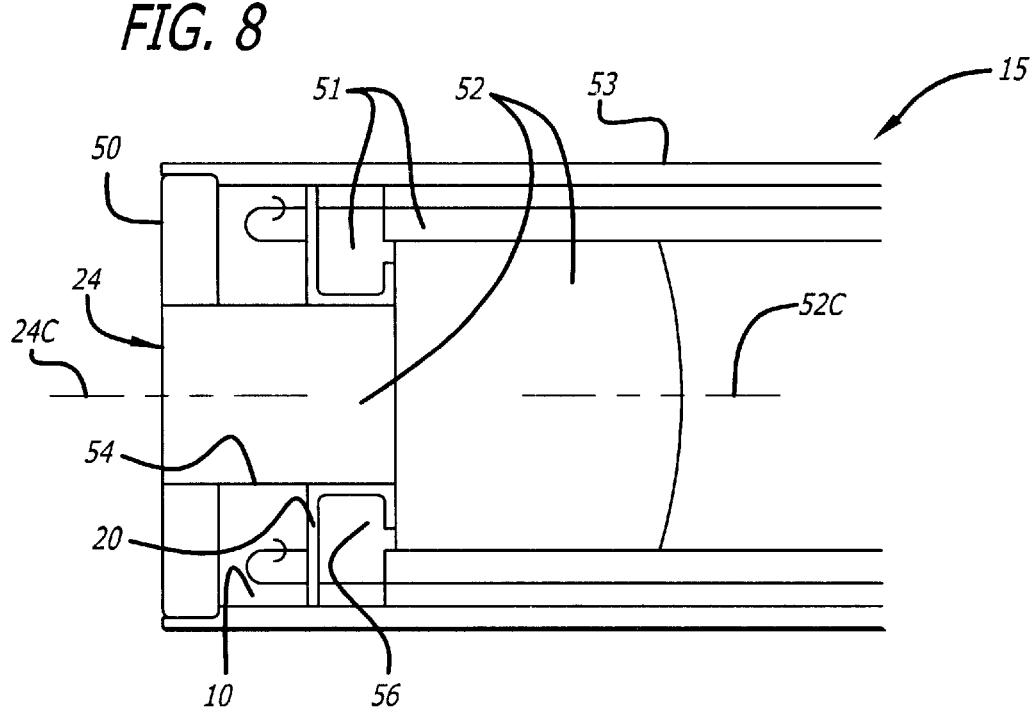
FIG. 8 is a cross-sectional side view of the distal end of the endoscope to which the present invention is mounted.

Looking first at FIG. 8, the illumination system of the present invention is shown, in which an illumination means 10, here an LED assembly, is adapted for mounting at the distal end of a 10 mm outside diameter endoscope 15, which is the typical size used in abdominal laparascopic procedures. As seen on FIG. 1, this first embodiment of illumination means 10 incorporates inner and outer rings of 28 individual LED chips or dies 22 mounted to separate reflector cups 21 which are then mechanically bonded to a base plate, which in this embodiment is an annular ceramic substrate 20. A cylindrical aperture 24 passes through the center of substrate 20, the aperture 24 and substrate 20 having a central axis designated as 24c.

As shown in FIG. 8, aperture 24 will have a diameter larger than the entrance pupil (not shown) of a conventional endoscope objective lens system 52 (having a central axis designated as 52c) and slightly less than stepped down section 54 of lens system 52. Typically, lens system 52 will have a 6 mm diameter and with an entrance pupil of approximately 3 mm diameter. Aperture 24 allows light reflected from the object being viewed to pass through assembly 10 to lens system 52 unhindered.

The outside diameter of substrate 20, typically 9 mm, is sized and configured to mate with the inside diameter of a stainless steel sheath 53 of endoscope 15 that houses illumination means 10 and objective lens system 52. An inner sleeve 51, preferably made of copper, lines the inner surface of sheath 53 and at its distal end, turns inward to form a base portion 56 to contact the proximal surface of substrate 20. Sleeve 51 acts as a heat sink for illumination means 10. To insure good thermal contact between substrate 20 and sleeve 51, a light coating of zinc oxide is applied to the proximal surface of substrate 20. A translucent protective window 50 is mounted distally of illumination means 10.

The LED assembly illumination means 10 as described herein has an efficiency of approximately 1.2 percent (light power output divided by electrical power input). This requires the dissipation of about 3.5 watts of thermal energy from the tip of endoscope 15. The heat dissipation is primarily by radiation and convection from stainless steel sheath 53. Although stainless steel is a poor thermal conductor (as compared to copper), copper cannot be used as the external sheath owing to its lack of biocompatability with the body. This and the size of the thermal load requires that substrate 20 contact copper inner sleeve 51 (see FIG. 8) to dissipate the thermal load along the full length of endoscope 15 with minimal gradient. Inner sleeve 51, preferably having a wall thickness of approximately 1.5 mm, thermally contacts stainless steel sheath 53 so that a very small temperature drop occurs from the outside surface of sleeve 51 to the outer surface sheath 53, thus allowing maximum radiated and convective heat dissipation from the stainless steel. Using this technique, the average temperature rise of endoscope 15 is held to 20 degrees centigrade for a thermal load of 3.5 watts. By contrast, the average temperature rise for an all stainless steel construction (including sleeve 51) exceeds 50 degrees centigrade and the distal tip temperature exceeds 90 degrees centigrade for an ambient temperature of 20 degrees centigrade.

Looking now at FIGS. 1–4, LED illumination means 10 is fabricated by first depositing in a conventional manner the metal required for interconnecting land and lead bond pad patterns onto the 0.5 mm thick, high purity alumina substrate 20. Next, reflector cups 21 are soldered to substrate 20. The LED die 22 are bonded in place to reflector cups 21 with a conductive epoxy, cathode 42 down for blue die 32 and green die 31 as shown on FIG. 4, and with anode 41 down for red die 30, as shown in FIG. 3. For red die 30, cathodes 42 are then lead bonded to their respective pads 44, using wire bonds 43, as are anodes 41 in the case of blue and green die 32, 31.

As seen on FIG. 2, six electrical connections must be made to illumination means 10: First and second red LED power connectors 33, 37, first and second green LED power connectors 34, 35, blue LED power connector 36, and ground connector 38. These six leads pass through their respective substrate cutouts 23 (FIG. 1) and then are soldered in place on the top or distal surface of substrate 20. Power is supplied to illumination means 10 from a battery pack (not shown) in the proximal end of endoscope 15.

Figure 5:
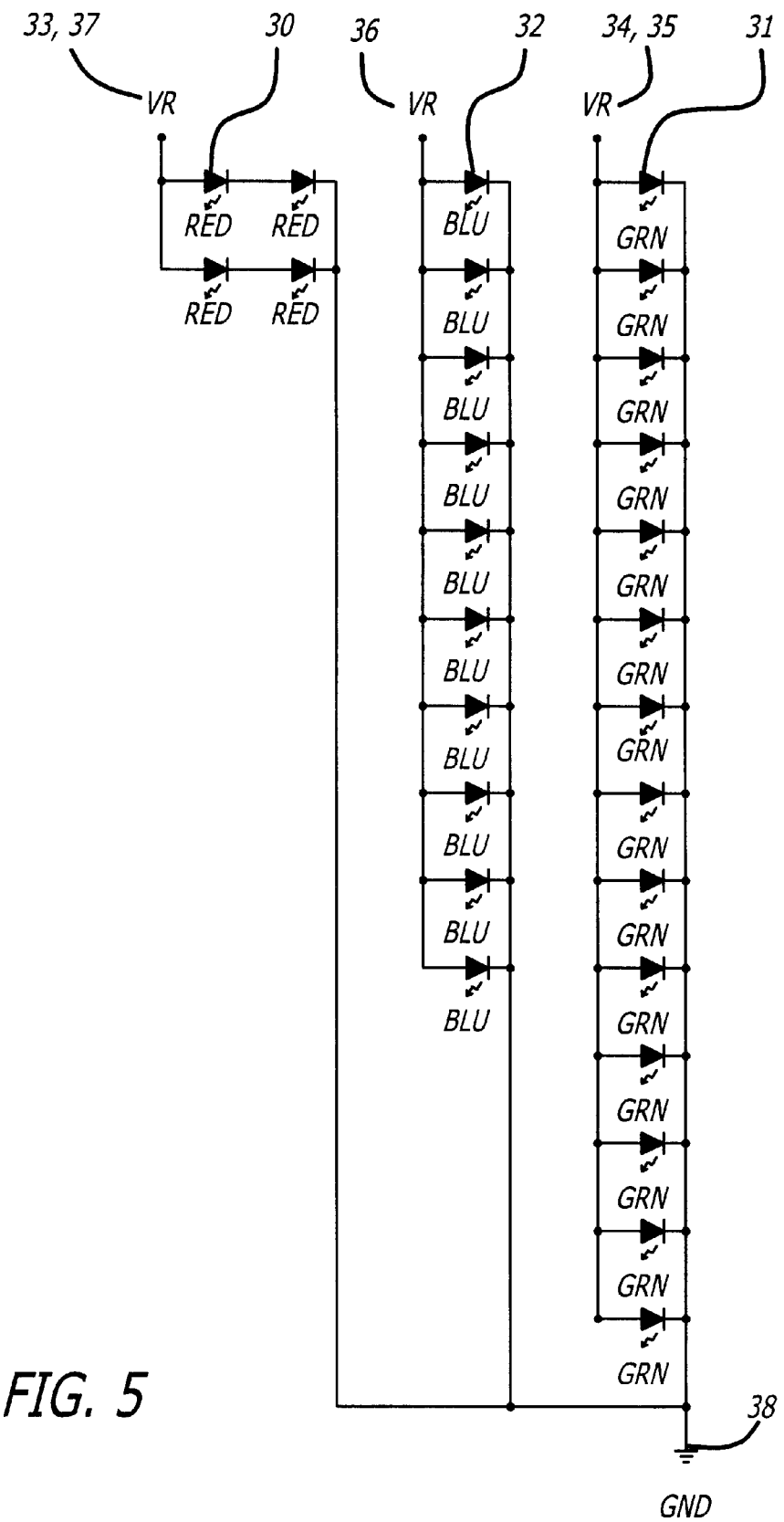
FIG. 5 is an electrical schematic diagram of the LED assembly.

In accordance with FIGS. 2 and 5, two each of two red die 30 are wired in series while the ten blue die 32 and fourteen green die 31 are wired in parallel. Owing to their higher efficiency, red LEDs 30 have a much smaller forward voltage drop than do blue or green LEDs 32, 31 at the same current. This wiring arrangement more nearly matches the voltage required to drive the three LED strings shown in FIG. 5, thus minimizing voltage transients as the camera timing function switches sequentially among and between the three colors. In a preferred embodiment of the illumination system, the supply voltage (VR) for red die 30 will be 3.9 V, with a total red LED current of 200 mA. The supply voltage for blue LED die 32 (VB) will be 5.5 V, at 1.2 A total blue LED current. Green LED die 31 will have a supply voltage (VG) of 3.3 V, at 1.2 A total current.

In choosing the number of each color of the LEDs required to adequately light a particular body cavity, the character of the object must be considered as well as the amplitude and spatial resolution of the three primary colors. It is known that the spatial resolution of the color components from a body cavity contain red data with high frequency variation, green data with little substantial variation, and blue data with intermediate frequency variation. Further, images from body cavities have very little blue amplitude component as compared with red and green.

Figure 9:
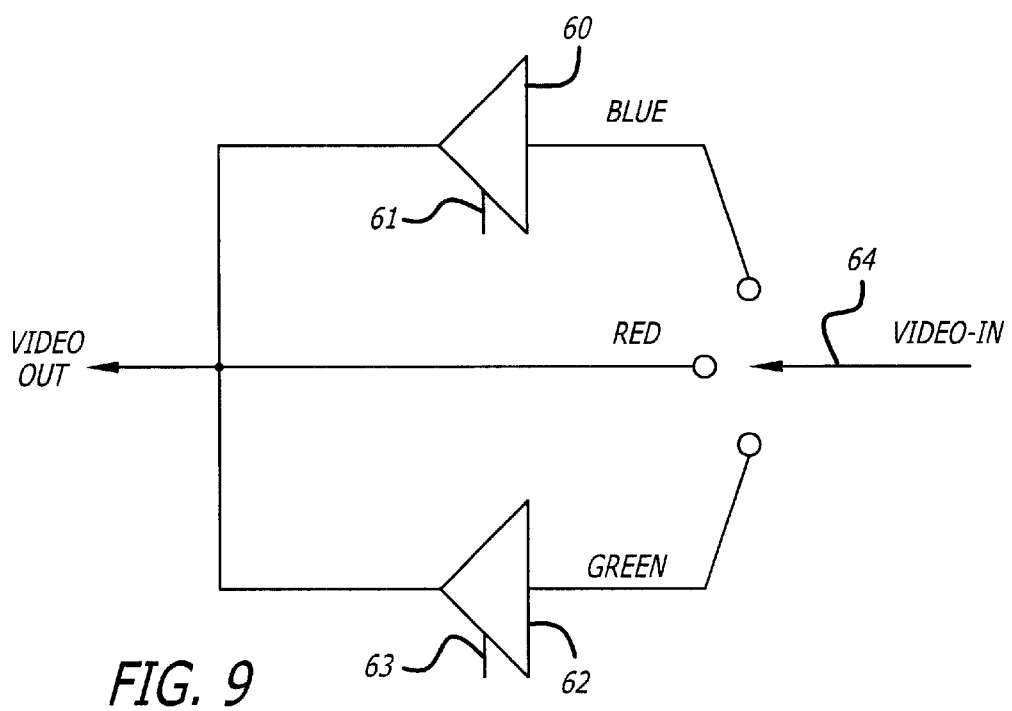
FIG. 9 is an electrical schematic of a circuit used for white balancing of the three colors emitted by the illumination system of the present invention.

The other factors that affect the number of die needed of each color are LED efficiency, CCD video detector quantum efficiency at each of the three wavelengths, and the needed signal-to-noise ratio. The circuit shown in FIG. 9 can be used in the system of the present invention to provide proper color balance. Using a switch 64 synchronized with the field switching circuit of the camera system described above, the video data input (as reflected from the object field into endoscope 15 is alternated between red, green, and blue positions. The red primary color input is not adjusted. Blue and green video amplifiers 60 and 62 are used to compensate and adjust the blue and green video levels, using amplifier gain control inputs 61 and 63. With a blue channel gain of approximately 28 dB (over the red channel), and a green channel gain of approximately 6 dB, using 4 AlGaAr red LED's 30, 14 GaP green LED's 31, and 10 silicon carbide blue LED's 32, driven in a one-third duty cycle at 100 ma peak current, results in a combined signal-to-noise ratio of approximately 35 dB at an object distance of 75 mm inside a typical abdominal cavity.

Prior art light sources typically deliver to the abdominal cavity 200 microwatts of optical energy per cubic centimeter of volume occupied by the light source, or about 60 milliwatts of optical power per pound of weight of the source. The LED assemblies 10 of FIG. 1 or FIGS. 13a and b can deliver 200 milliwatts per cubic centimeter of volume or 5 watts per pound of weight. Since the single sensor sequential camera described above requires approximately 5 to 10 milliwatts of light output, the illumination system of the present invention can be made small and light in weight as compared to the prior art, thus allowing it to be highly portable and installed in the distal end of an endoscope.

Figure 7:
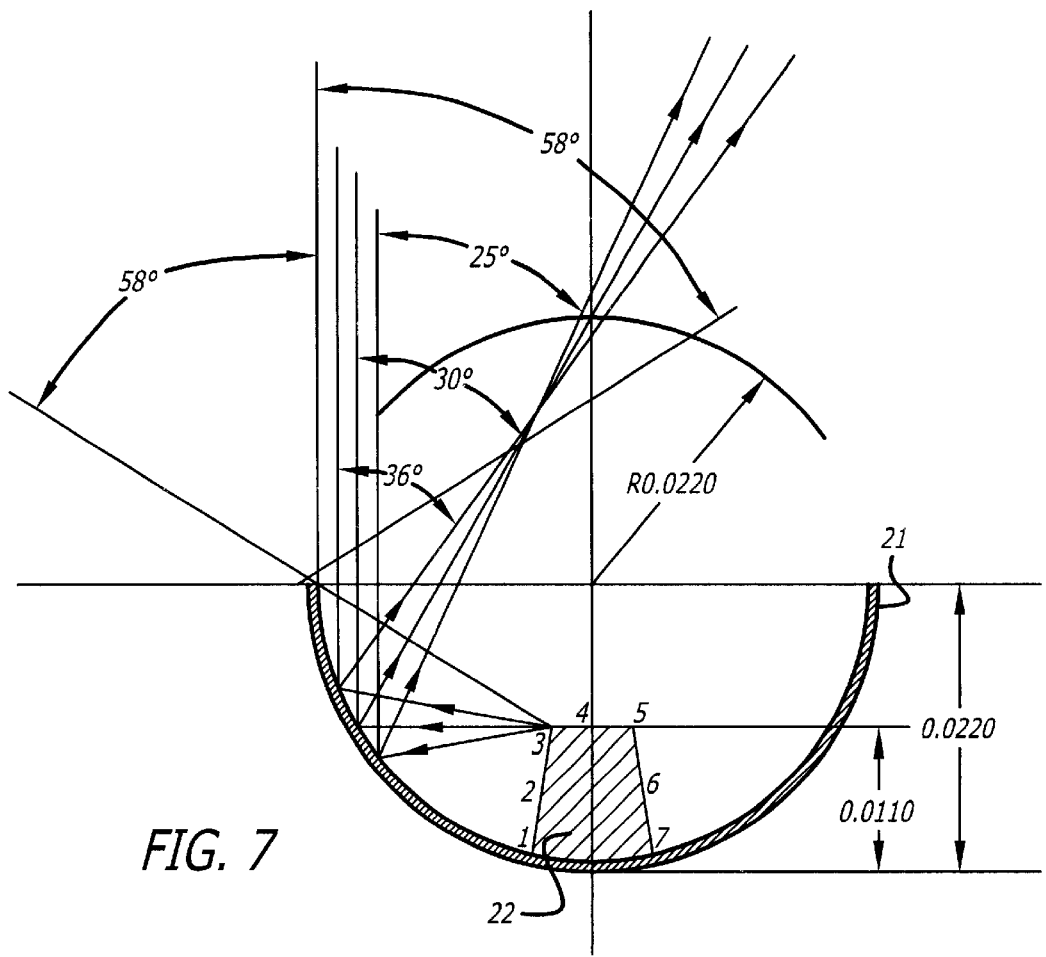
FIG. 7 is a side view of a single LED chip or die mounted within a reflector cup, further showing the angles of light emitted from and reflected therein.

The power distribution of the light from endoscope 15 should be as homogenous as possible to insure adequate lighting in all zones of the image and, in the case of sequential cameras, the three colors should be coincident to avoid chromatic effects. FIG. 7 shows a side view of a typical LED die 22 positioned within a reflector cup 21. LED die 22 is almost cubic in shape, with each dimension being approximately 250 microns. Actually, most die are slightly trapezoidal in shape, being somewhat larger at the base than at the top. The horizontal cross sections are usually square. Light is emitted from the top edges 3 and 5 of die 22, primarily in a small horizontal angular cone and from the top surface 4 in, more or less, a cosine distribution. The fraction of the light emitted from the edges as compared to the top surface depends on the technology used in constructing die 22. Typically, for a blue LED 32 made of a silicon carbide die, the edge emission accounts for 80 percent of the total light output. Thus, mounting each die 22 in a separate reflector cup 21 can serve to control the angular emission of a significant portion of the light. FIG. 7 depicts a die 22 mounted such that the edge emission is located in a 20 degree cone centered at the focus of a hemispherical reflecting cup 21. It can be seen that the rays are redirected into a 36 degree cone about the vertical axis. The reflected light adds to the light emitted from the top surface 4 of die 22. If LED die 22 were used without reflecting cup 21, none of the edge emitted light would reach the object field.

Figure 6A:
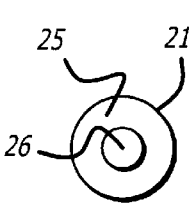
FIG. 6a is top view of the reflector cup used in conjunction with each of the LED's of the present invention.
Figure 6B:
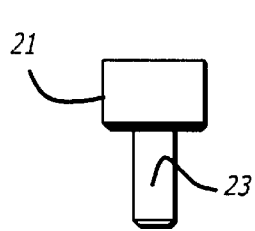
Figure 6C:
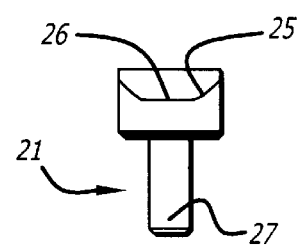
FIG. 6c is a cutaway side view of the reflector cup of FIGS. 6a and 6b.

Control of the depth of mounting of die 22 within reflector cup 21 gives a considerable degree of control on the dispersion angle. Moving die 22 lower or higher than the focal point of reflector cup 21 dramatically increases the angular dispersion. FIGS. 6a, b, and c illustrate a preferred geometry of reflector cup 21 which is molded of very high purity alumina to have a flat, centrally disposed die mounting surface 26 with a 0.6 mm to diameter, located approximately 0.4 mm below the top of cup 21. A concave section 25 surrounds surface 26 and extends upwardly and outwardly a linear distance of approximately 0.68 mm, thereby defining an outer diameter of cup 21 of approximately 1.3 mm. The radius of curvature of concave section 25 is approximately 0.56 mm. An integrally formed post 27 facilitates mechanical attachment of 21 to substrate 20.

FIGS. 10–13 illustrate an alternate embodiment of LED illumination means 10 in which reflector cups 21 are molded into ceramic substrate 20. Electrical interconnections are made by first metal depositing the entire top or distal surface of substrate 20 and etching away the areas that are not electrically connected, leaving the wire bond pattern shown on FIG. 11a. LED die 22 are then bonded to die mounting surface 26 of reflector cups 21, as seen in FIGS. 12a and b. Lead bonding to the LED die is accomplished in the same manner as shown in FIGS. 3 and 4, resulting in illumination means 10 shown in FIGS. 13a and b.

Figure 14:
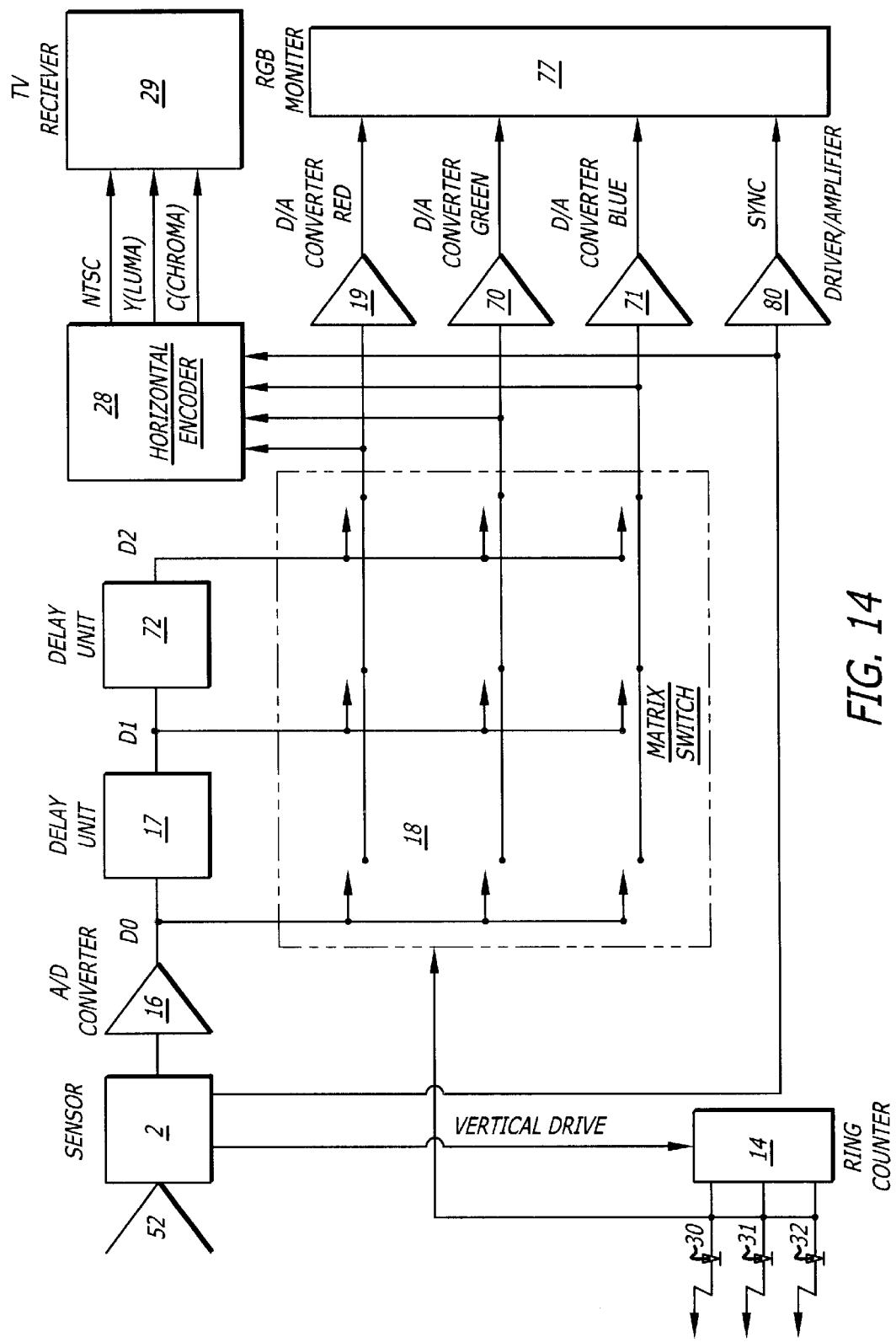
FIG. 14 is a block diagram of a single sensor sequential video imaging system used in conjunction with the illumination system of the present invention.

The illumination system described above is ideally suited for use with applicant's "Single Sensor Video Imaging System and Method Using Sequential Color Object Illumination", described in detail in co-pending U.S. patent application Ser. No. 905,278, the specification and drawings of which, as amended, are incorporated herein by reference. Referring to FIG. 14, there is shown by block diagram representation a field sequential video imaging system in combination with the illumination system of the present invention, as well as the basic method by which an object to be viewed is illuminated and color video image data is processed. The method begins by illuminating an object (not shown) with light from a first primary color light source, red LED 30 for example, for a period of time typically equal to a standard television field period. Conventionally, this period is 1/60 second. Red LED 30 is activated for this field period by one of three outputs from the divide by three ring counter 14, which has been selected by the vertical drive signal of the sensor 2 in endoscope 15, preferably a conventional charge coupled device (CCD) assembly, such as the model CCB/M27 from Sony Corporation of America. However, any appropriate photo sensor array can be used. The light reflected from the object is focused onto sensor 2 by lens system 52, also of conventional design.

At the end of the first field period, the vertical drive signal makes a transition and thereby selects the second output of the ring counter 14, resulting in the deactivation of red LED 30 and the activation of a second primary light source, green LED 31 for example, for one field period. During this second field period, analog data measuring the response of sensor 2 to light reflected from red LED 30 is captured by analog-to-digital (AID) converter 16 while integration of the second signal (from green LED 31) is occurring in sensor 2. The output from A/D 16 is provided both to a first digital delay unit 17 and a matrix switch 18. First delay 17 delays the digitized signal for a time period equal to one field period.

The output signals of ring counter 14 are timed and synchronized such that matrix switch 18 connects the output of A/D 16 (reference D0) to first digital-to-analog converter (DAC) 19. First DAC 19 converts the first captured and digitized primary color signal corresponding to the first primary color, from red LED 30, back to analog form, to be used as the odd field video data of the first primary color signal, red for example.

Following the second field period, the object is illuminated by a third primary color light source, blue LED 32 for example, for a third period of time equal to a field period. This is accomplished by the vertical drive signal from the sensor 2 making a transition, thereby deactivating green LED 31 and activating blue LED 32. During this third field period, the third primary color light reflected from the object is focused onto sensor 2. Simultaneously with integration of the third primary color signal in sensor 2, the analog video signal corresponding to the level of reflected second primary color light is captured and digitized by A/D 16. At the beginning of this third field period, the outputs of the ring counter 14 are in such a state as to connect the output from the A/D 16 (D0) to a second DAC 70, and the output from first delay 17 (D1) to first DAC 19. Thus, response of the sensor 15 to the first primary color signal, from red LED 30, is again presented at the output of first DAC 19 for the even field period of the first primary color. The output of second DAC 70 is the analog video signal corresponding to the second primary color from green LED 31.

Following the third field period, the object is again illuminated with red LED 30 for a fourth period of time equal to a standard field period. This is accomplished by the vertical drive signal of sensor 2 making a transition which causes green LED 32 to be deactivated and red LED 30 to again be activated. The third color analog signal is captured from sensor 2 and digitized by the A/D 16 during this fourth field period, while the first color light signal is again being integrated.

The second color captured and digitized signal is delayed by first delay 17 and the first color digitized signal is further delayed by one field period by a second delay unit 72. At the beginning of the fourth field period, the outputs of ring counter 14 are such that A/D 16 output (D0) is connected to a third DAC 71, the output of the first delay 17 (D1) is connected to second DAC 70, and the output of second delay 72 (D2) is connected to first DAC 19. Also during this fourth field period, the second color digital signal is reconverted to analog format by second DAC 70 and becomes the odd field of the second color signal. Likewise the captured digitized third primary signal (not delayed) is reconverted to analog format by third DAC 71 and becomes the odd field of the third color video signal.

The process continues, in the manner previously described, with repeated successive second, third, and fourth illumination periods. It will be apparent to those skilled in the art that the first field or illumination period is operationally identical to the seventh illumination period, except that the first illumination period begins with sensor 2 and related devices in a starting or "0-state" condition. It should be noted that if precise field period analog delay lines were available it would not be necessary to digitize the output of sensor 2 and then reconvert it to analog format. Rather, the sequential analog signals could be merely switched by matrix switch 18 to their respective color signal outputs.

The output signals from DAC's 19, 70, and 71, after processing in the manner described, now correspond to standard video signals capable of display by a conventional RGB color television monitor 77, in conjunction with a standard television synchronization signal obtainable from sensor 2, through sync driver-amplifier 80. Accordingly, in the preferred embodiment, the resulting video image will comprise conventional odd and even frames or fields of data comprising typically 262.5 horizontal lines each which are interlaced and displayed for one standard field period (1/60 second) each, producing a completed television video image of 525 horizontal lines.

As an alternative to using an RGB monitor, the digitized primary color signals and sync signal can be sent to the inputs of a standard NTSC format modulator/encoder unit 28, for display on a standard NTSC format television receiver 29.

To obtain conventional chrominance and luminance color video signals, red LED's 30 can be activated simultaneously with green LED's 31 during periods which are sequentially interspersed between periods of separate illumination by red LED's 30 and blue LED's 32. The reflected light from the object resulting therefrom is then used to obtain signal levels from which chrominance and luminance signals can be calculated and generated in manner well known to those skilled in the art.

Figure 15:
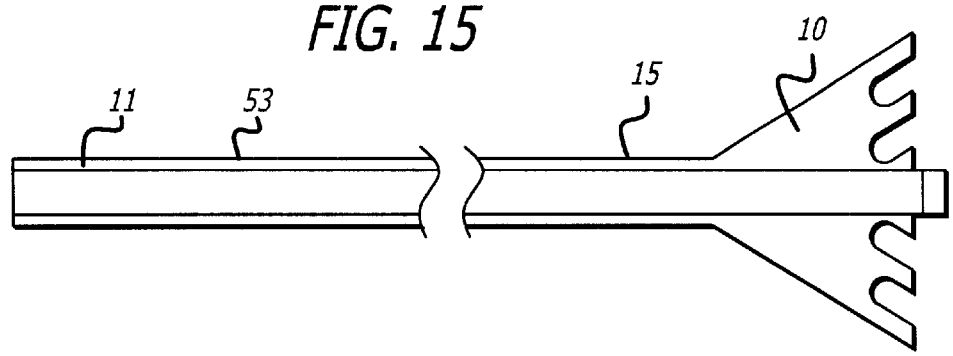
FIG. 15 is a side view of second embodiment of the illumination system in which an LED assembly is mounted in the camera head, with light transmitted to the distal end of the endoscope via optical fibers or plexiglass.

FIG. 15 illustrates a second embodiment of the illumination system of the present invention in which illumination means 10 includes both an LED assembly or other light source mounted at the proximal or camera head end of endoscope 15 and a light transmission means, such as fiber optic cables 11 which extend along sheath 53 to the distal end of endoscope 15.

Figure 16:
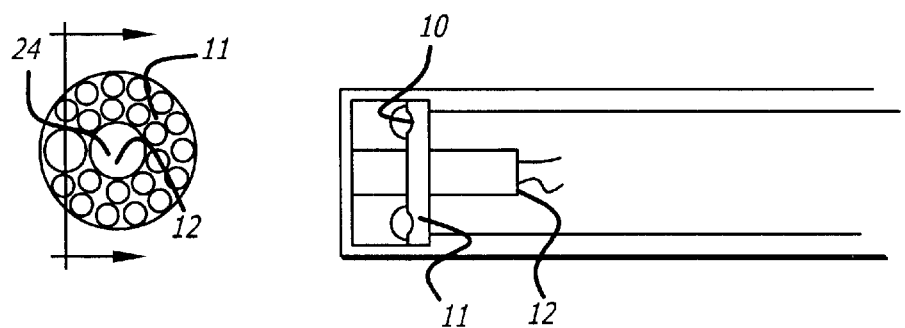
FIG. 16 is a cutaway side view of a third embodiment of the illumination means in which an LED assembly is combined with a white light source at the distal end of the endoscope.

FIG. 16 shows another embodiment of the illumination system in which illumination means 10 includes both an LED assembly 11 and a white light source 12 which extends through aperture 24 of assembly 11. White light source 12 could be a Xenon tube, for example, which can be pulsed to conform with sequential color illumination requirements. Thus, by placing a blue filter in front of white light source 12, blue light can be obtained and low efficiency blue LEDs could be eliminated from LED assembly 11.

Figure 17:
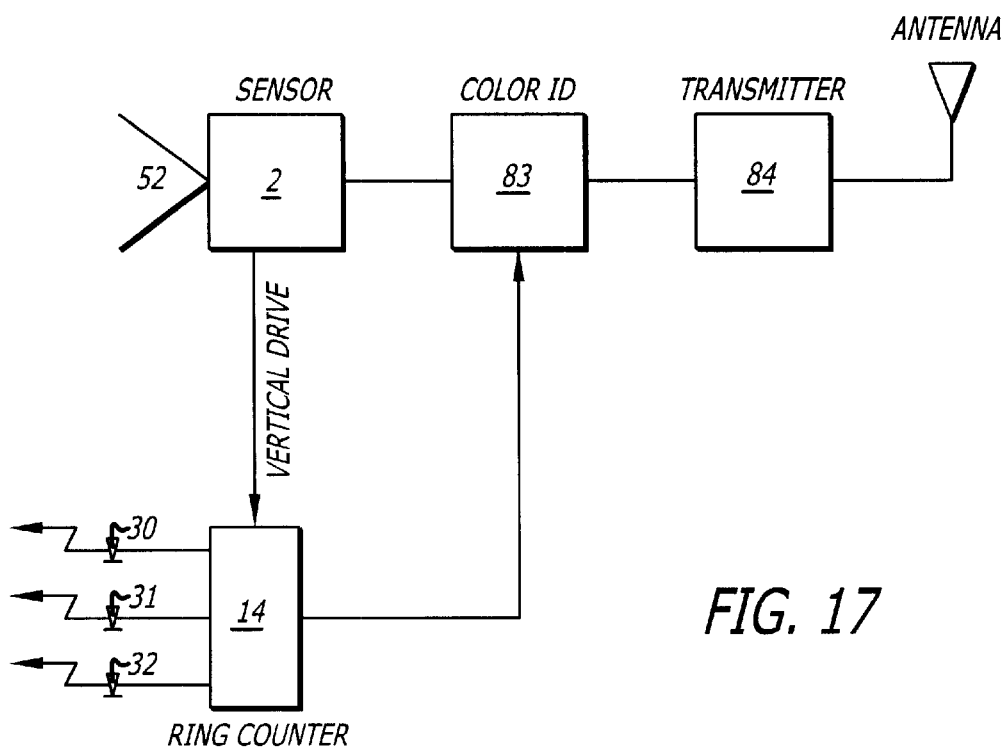
FIG. 17 is a block diagram of the video head-transmitter unit of a fourth embodiment of the present invention, in which analog video data is transmitted to a remotely located receiver-processor unit.
Figure 18:
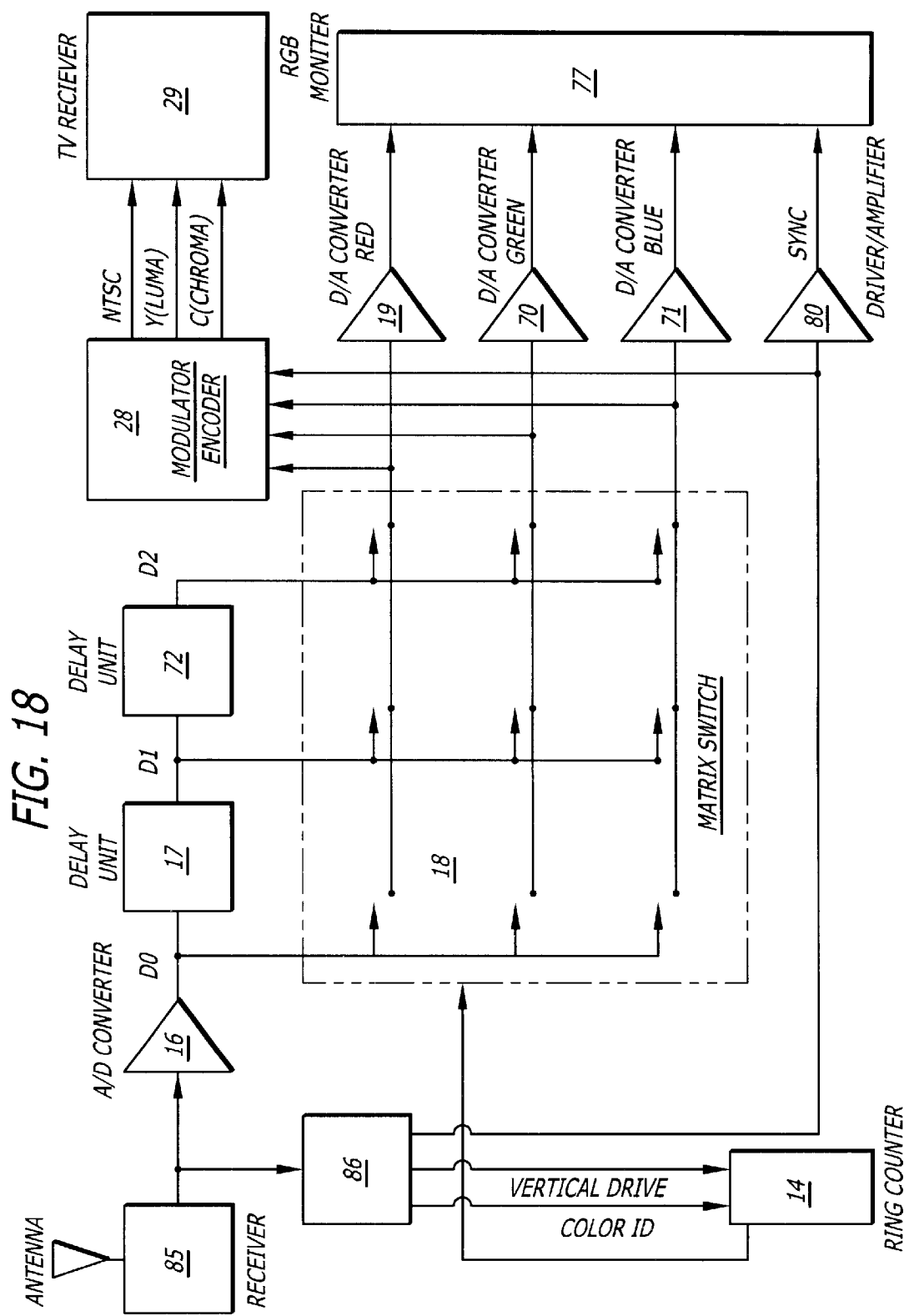
FIG. 18 is a block diagram of the receiver-processor unit of the fourth embodiment of the present invention.

Referring to FIGS. 17 and 18, a fourth embodiment of the apparatus of the present invention is shown in which a separate light source/sensor unit (FIG. 17) includes a transmitter for sending analog color level signals to a remote receiver-processor unit (FIG. 18). In this embodiment, data from sensor 2 is tagged with a color identifier signal from ring counter 14 by means of a conventional add color ID circuit 83. which tags the video signal with an identifying pulse denoting which primary color is then represented by the video signal. The output of the add ID circuit 83 is then coupled to a wireless transmitter 84 (also of conventional design) from which it is transmitted to a remote site. Add ID circuit 83 and transmitter 84 can be incorporated in the device either prior to or after A/D 16. In the former case the transmission is of analog video data and in the latter case digital data is transmitted. A conventional color sync signal is also transmitted.

Referring now to FIG. 18, the transmitted data is then received by conventional wireless receiver 85. A conventional sync separator circuit 86 strips off the television synchronization signal. the vertical drive signal, and the color ID signal. The latter two signals control ring counter 14 for selecting the appropriate connections to DAC units 19, 70, and 71. Otherwise the method is identical to that described with reference to the first embodiment of FIG. 1.

Figure 19:
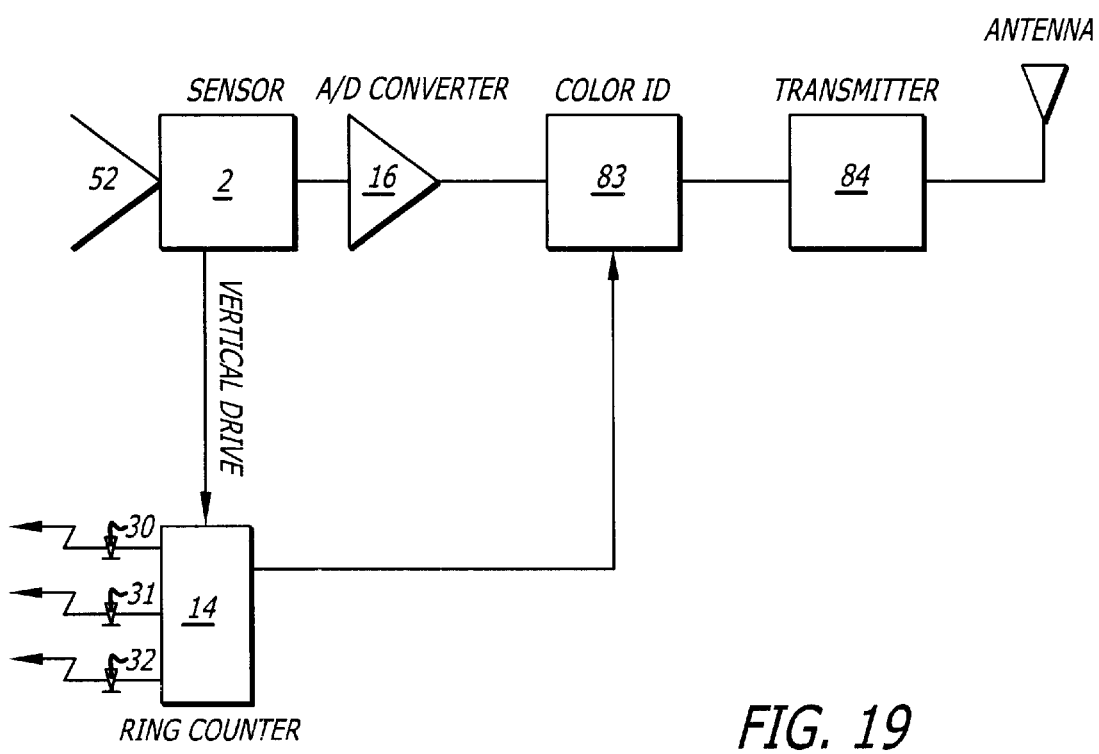
FIG. 19 is a block diagram of the video head-transmitter unit of a fifth embodiment of the present invention in which data is digitized and transmitted to a remote receiver-processor unit.
Figure 20:
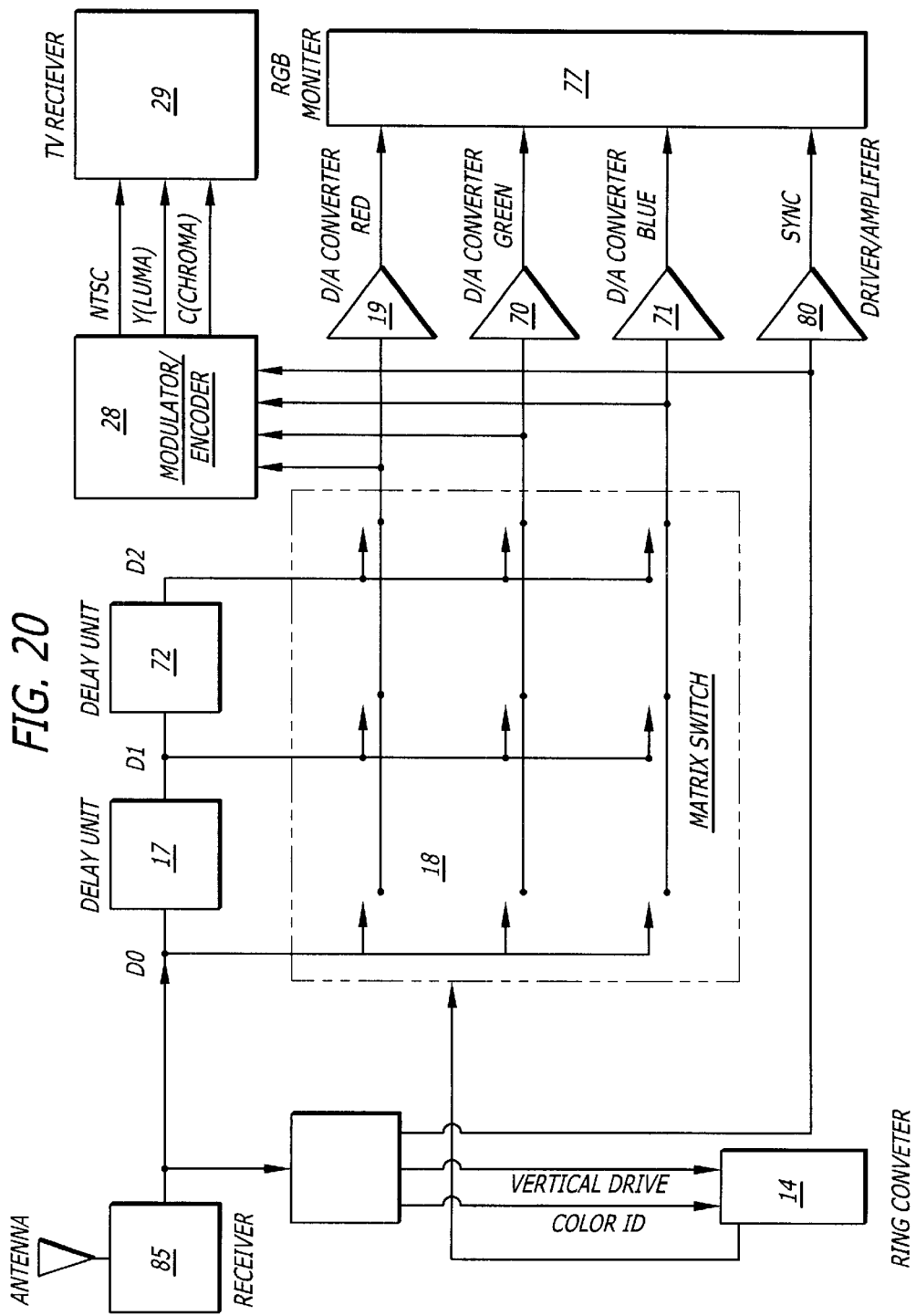
FIG. 20 is a block diagram of the receiver-processor unit of the fifth embodiment of the present invention.

FIGS. 19 and 20 show yet a fifth embodiment of the present invention in which the apparatus of FIGS. 17 and 18 is modified by relocation of A/D 16 such that transmission of digital rather than analog data occurs between the transmitter and receiver.

Thus, although there have been described particular embodiments of the present invention of a new and useful LED Illumination System for Endoscopic Cameras, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. An endoscopic camera in combination with an illumination system comprising:
   a. a sheath;
   b. illumination means mounted at the distal end of said sheath;
   c. a video detector;
   d. an objective lens system mounted within said sheath between said illumination means and said video detector; and
   e. the illumination means comprising a plurality of light emitting diodes arranged in a generally concentric pattern surrounding a light transmissive central aperture in the center of said pattern, said central aperture having a central axis aligned with and coaxial with a central axis of said objective lens system and with a central axis of said sheath.

2. The endoscopic camera and illumination system combination of claim 1 further comprising means to activate said illumination means in synchronization with said video detector whereby said illumination means illuminates a body cavity proximate said camera with sequences of colored light.

3. An endoscopic video camera system comprising:
   a. an illumination system for sequentially illuminating an object, said illumination system including an illumination means having first, second, and third primary color light sources, said illumination means mounted at the distal end of a camera sheath, the illumination means comprising a plurality of light emitting diodes arranged in a generally concentric pattern surrounding a light transmissive central aperture, said central aperture having a central coaxially aligned with a central axis of said camera sheath;
   b. means for separately and successively activating said first, second, and third primary color light sources for equal standard television field periods;
   c. means for focusing a primary color light reflected from said object onto a sensor, said sensor providing a primary color level analog data responsive to the level of said primary color light focused onto said sensor;
   d. means for capturing said primary color level analog data from said sensor;
   e. A/D converter means for converting said captured primary color level analog data to digital format, thereby providing digitized captured primary color level data;
   f. first delay means coupled to the output of said A/D converter means for delaying for a standard television field period said digitized captured primary color level data;
   g. second delay means coupled to the output of said first delay means for further delaying for a standard television field period said digitized captured primary color level data;
   h. first, second, and third digital-to-analog converter means for converting said digitized captured primary color level data from said A/D converter means, from said first delay means, and from said second delay means, thereby providing reconverted first, second, and third primary color level analog data, said re-converted first, second, and third primary color level analog data representing color television video signals corresponding to said first, second, and third primary colors; and
   i. means for successively switching the outputs of said A/D converter means said first delay means, and said second delay means to said first, second, and third digital-to-analog converter means.

4. The system of claim 3 further comprising monitor means operatively connected to the outputs of said first, second, and third digital-to-analog converter means.

5. The apparatus of claim 4 further comprising means for wireless transmission of said primary color level analog data from said sensor to a remote location.

6. A compact light source for illuminating an object while in a body cavity, said light source comprising first, second, and third color LED's fixed to a common substrate, said first, second, and third color LED's electrically connected to said substrate and to each other in a pattern whereby said first, second and third color LED's can be separately operated in a sequential manner; said first, second, and third color LED's arranged in a generally concentric pattern surrounding a light transmissive aperture centrally disposed in said substrate in the center of said pattern and said substrate and aperture having a central axis coaxial with a central axis of an objective lens system of an endoscopic camera used in conjunction with said compact light source.

7. The light source of claim 6, further comprising circuit means to operate said first and second color LED's simultaneously whereby chrominance and luminance color video signals can be generated from light reflected from the object being viewed.

8. An endoscopic video camera system comprising:
   a. a video camera mounted at the proximal end of an endoscope; and
   b. illumination means for emitting light from said system toward an object be viewed within a body cavity, said illumination means mounted within the distal end of said endoscope, said illumination means comprising a plurality of LED's mounted to a ceramic substrate in an annular pattern surrounding an aperture centrally formed in said pattern and in said substrate whereby said substrate and aperture have a central axis coaxially aligned with a central axis of said endoscope.

9. The camera system of claim 8 further comprising means for re-directing light emitted from the edges of each of said LED's toward the object to be viewed.

10. A video camera for viewing objects in a body cavity, the camera comprising:
   a. light source means to illuminate the object with light;
   b. video sensor means to electronically capture the light reflected from the object and to generate video data representing an image of the object;

c. an optical lens system having a distal and a proximal end, the proximal end adjacent to the video sensor means;

d. transmitter means for wireless transmission of the video data from the video sensor means to a remote receiver; and e. the optical lens system enclosed in an optical head of the camera, the optical head having a shape and size whereby the head can be endoscopically inserted and positioned within the body cavity, the light source positioned in the optical head and comprising a plurality of light emitting diodes arranged in a generally concentric pattern surrounding a light transmissive central aperture in the center of said pattern, said central aperture and said pattern of light emitting diodes having a central axis coaxially aligned with a central axis of the optical lens system.

11. The video camera of claim 10 wherein the light source means is positioned at a distal end of the optical lens system and within the optical head.

12. The video camera of claim 10 wherein the light source means is located in a camera body separated from the optical head, the camera further comprising a fiberoptic connection between the light source means and the optical head.

13. The camera of either claims 11 or 12 further comprising means to digitize the video data before it is transmitted to the remote receiver.

14. The video camera of claim 10 wherein the light source means comprises a light emitting device and at least one color filter.

15. The video camera of claim 10 further comprising means for controlling light angularly emitted from the light emitting diodes.

16. The video camera of claim 10 wherein the light source means comprises a xenon bulb.

17. The video camera of claim 10 wherein the light source means comprises means for sequentially illuminating the object with light from separately activated first, second, and third primary color light emitting devices.

* * * * *

UNITED STATES PATENT AND TRADEMARK OFFICE
CERTIFICATE OF CORRECTION

PATENT NO.     : 6,449,006 B1
DATED          : September 10, 2002
INVENTOR(S)    : John I. Shipp It is certified that error appears in the above-identified patent and that said Letters Patent is hereby corrected as shown below:

<u>Column 9,</u>
Line 10, after "central" (first occurrence) insert -- axis --.

<u>Column 10,</u>
Line 13, change "reconverted" to -- re-converted --;
Line 19, after "means" (first occurrence) insert -- , --.
Line 26, change "apparatus" to -- system --.
Line 38, after "pattern" insert -- , --.
Line 51, after "object" insert -- to --.

Signed and Sealed this

Twenty-fifth Day of February, 2003

JAMES E. ROGAN
*Director of the United States Patent and Trademark Office*